(12) United States Patent
Patire

(10) Patent No.: US 6,826,784 B2
(45) Date of Patent: Dec. 7, 2004

(54) CONTROLLED SIGHT DEVICE

(76) Inventor: Thomas J. Patire, 281 Rte. 46 West, Elmwood Park, NJ (US) 07407

( * ) Notice: Subject to any disclaimer, the term of this patent is extended or adjusted under 35 U.S.C. 154(b) by 60 days.

(21) Appl. No.: 10/206,979

(22) Filed: Jul. 30, 2002

(65) Prior Publication Data

US 2004/0019948 A1 Feb. 5, 2004

(51) Int. Cl.⁷ .................................................. A61F 9/02
(52) U.S. Cl. ................ 2/433; 2/15; 128/858; 351/46
(58) Field of Search ............... 2/15, 433, 10, 2/12; 128/857, 858

(56) References Cited

U.S. PATENT DOCUMENTS

| | | |
|---|---|---|
| 2,045,399 A | 6/1936 | McMurdo |
| 2,305,080 A | 12/1942 | Hemphill et al. |
| 2,537,768 A | 1/1951 | Laporte |
| 2,690,173 A | 9/1954 | Seeger et al. |
| 2,721,322 A | 10/1955 | Harper |
| 3,487,549 A | 1/1970 | Engesser |
| 3,555,563 A * | 1/1971 | Grossman ...................... 2/433 |
| D253,198 S | 10/1979 | Posey, Jr. |
| 4,649,908 A | 3/1987 | Ghaly |
| 4,712,254 A | 12/1987 | Daigle |
| 4,790,031 A * | 12/1988 | Duerer ........................... 2/439 |
| 4,811,430 A | 3/1989 | Janusz |
| 4,852,882 A | 8/1989 | Otsuka et al. |
| 4,872,217 A | 10/1989 | Kitayama |
| 4,969,649 A | 11/1990 | Lugiewicz |
| 4,991,849 A | 2/1991 | Fabanich |
| 5,050,982 A | 9/1991 | Meissner |
| 5,072,724 A | 12/1991 | Marcus |
| 5,123,116 A * | 6/1992 | Roth ............................... 2/15 |
| 5,169,384 A | 12/1992 | Bosniak et al. |
| 5,171,152 A | 12/1992 | McCleery |
| 5,305,027 A | 4/1994 | Patterson |
| 5,343,561 A | 9/1994 | Adamo |
| 5,394,564 A | 3/1995 | Rodriguez |
| 5,413,346 A | 5/1995 | Hedlund et al. |
| 5,488,438 A | 1/1996 | Cochran |
| 5,489,953 A | 2/1996 | Griffith |
| 5,675,398 A | 10/1997 | Moore |
| 5,682,220 A | 10/1997 | Sherman et al. |
| 5,752,887 A | 5/1998 | Baldwin, IV |
| 5,818,569 A | 10/1998 | Berent |
| 6,067,664 A | 5/2000 | Cortes |
| 6,155,995 A | 12/2000 | Lin |
| 6,257,893 B1 | 7/2001 | Trabut |
| 6,571,799 B1 * | 6/2003 | Daly ........................... 128/857 |

\* cited by examiner

Primary Examiner—Katherine Moran
(74) Attorney, Agent, or Firm—Millen, White, Zelano & Branigan, P.C.

(57) ABSTRACT

An eye shield assembly useful in training students in non-deadly force, firearms and martial arts has an opaque first eye shield which is coupled to an apertured second eye shield by connecting together adjustable straps on both eye shields. One eye shield covers the eyes while the other eye shield forms a portion of the head strap. The opaque first eye shield simulates substantial or complete blindness while the apertured second eye shield simulates tunnel vision, both conditions being possible during an encounter with an adversary. By utilizing the eye shield assembly, the trainee becomes acclimated to sight impairment and learns to employ the skills obtained by his or her training in situations where there is sight impairment.

13 Claims, 2 Drawing Sheets

CONTROLLED SIGHT DEVICE

FIELD OF THE INVENTION

The present invention relates to devices for controlling sight. More particularly, the present invention relates to devices for restricting sight to facilitate training of students in sight restricted situations.

BACKGROUND OF THE INVENTION

In training people to contend with adverse situations by employing techniques such as non-deadly force or other techniques, such as martial arts and even firearms or other weapon use, it is important that trainees are able to function in situations where sight is compromised. For example, sight may be completely blocked or may be partially blocked, such as when a person under stress responds with temporary tunnel vision in order to focus only on a perceived immediate threat. Total blindness may occur simply because a confrontation is in the dark, or because an adversary has done something to intentionally or even unintentionally blind the person employing the force. Full sight, blindness and/or tunnel vision may occur in any order and for various durations during a confrontation. Consequently, it is desirable for a trainee to be able to function effectively when blinded or when startled in a way that causes tunnel vision.

SUMMARY OF THE INVENTION

With the aforementioned considerations in mind, the present invention is directed to an eye shield assembly for covering a user's eyes. The assembly comprises a first eye shield which is opaque and which has head strap portions extending from opposite ends thereof and a second eye shield having apertures therein for alignment with eyes, and also having head strap portions extending from opposite ends thereof. The first and second eye shields individually cover the eyes separately, with the eye shield not covering the eyes functioning as a portion of the headband for the entire eye shield assembly while the other eye shield covers the eyes.

In a further aspect of the invention, the head strap portions on the first eye shield and the head strap portions on the second eye shield cooperate to form an adjustable head strap arrangement.

In still a further aspect of the invention, head strap portions on the first eye shield and the second eye shield separate from one another and joined by couplings, the couplings preferably being of VELCRO® hook and loop material.

In still a further aspect of the invention, headband has elastic portions.

In still another aspect of the invention, second eye shield has a section for covering each eye wherein there is but a single aperture in each section for simulating tunnel vision.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
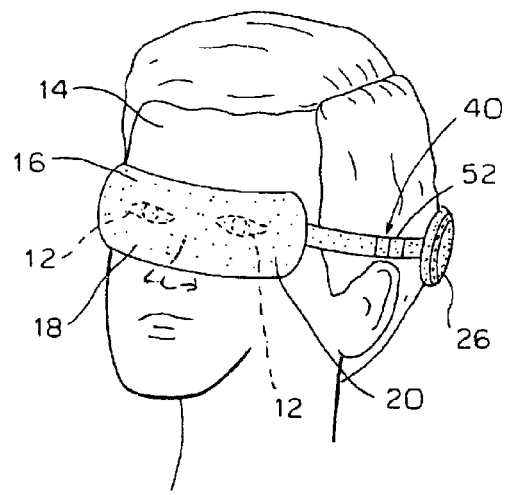
FIG. 1 is a perspective view showing an eye shield assembly in accordance with the present invention positioned with a first eye shield over a trainee's eyes to simulate complete blindness.

Referring now to FIG. 1 there is shown an eye shield assembly 10, configured in accordance with the present invention, positioned to simulate complete blindness by covering the eyes 12 of a trainee 14 with an opaque first eye shield 16 having first and second opaque sections 18 and 20. The purpose of the arrangement in FIG. 1 is to simulate complete blindness during training such as non-deadly force training, martial arts training or firearms training. It is desirable that one still be able to employ techniques learned during the training period even if for some reason sight is substantially or totally interrupted.

Figure 2:
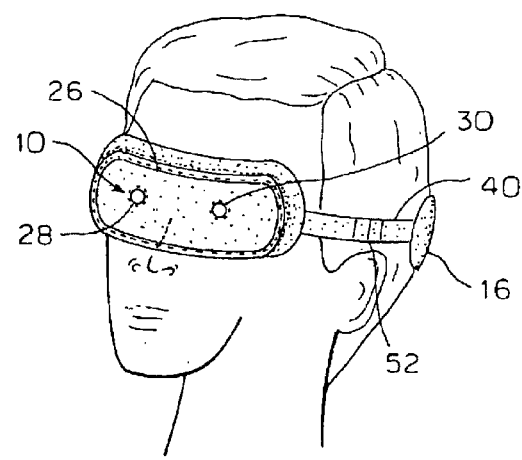
FIG. 2 is a perspective view similar to FIG. 1 but showing second eye shield of the eye shield assembly positioned over a trainees eyes to simulate tunnel vision.

Referring now to FIG. 2, the trainee 14 has the eye shield 10 positioned so that an apertured second eye shield 26 is positioned over the eyes 12, wherein the second appertured eye shield 26 has a pair of apertures 28 and 30 aligned with the eyes in order to simulate tunnel vision. Tunnel vision can occur when a person is subjected to stress due to a physical or mental threat. It is desirable that a person still be able to employ the techniques learned during training when impaired with tunnel vision.

Figure 3:
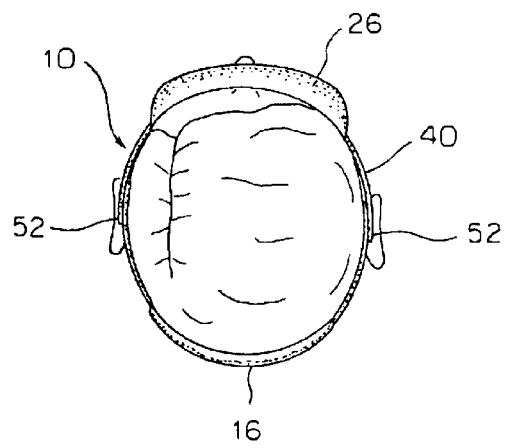
FIG. 3 is a top view of the eye shield assembly of FIGS. 1 and 2 shown mounted on a trainee's head.
Figure 4:
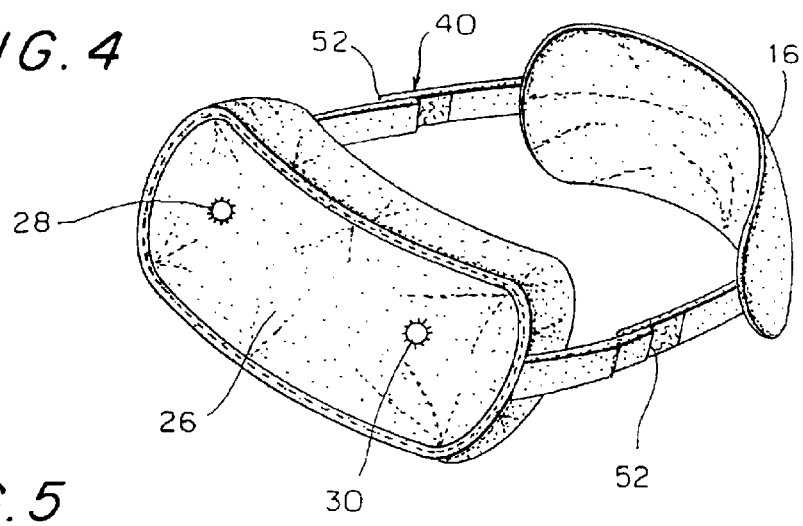
FIG. 4 is a perspective view of an eye shield assembly of the present invention.

Referring now to FIGS. 3 and 4, it is seen that the eye shield assembly 10 is a single unit with a head strap arrangement 40 connecting the opaque eye shield 16 and the apertured second eye shield 26 at the ends of the eye shields. Consequently, the entire assembly 10 is worn with either the opaque or apertured eye shield in place over the eyes 12 and with the other eye shield simply functioning as part of the head strap 40.

Figure 5:
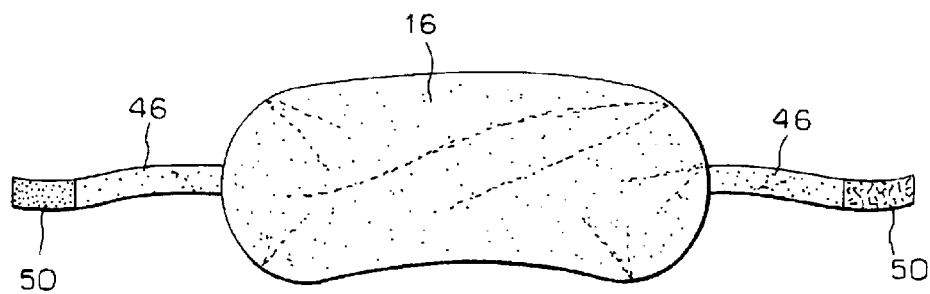
FIG. 5 is a perspective view showing the first eye shield separately.
Figure 6:
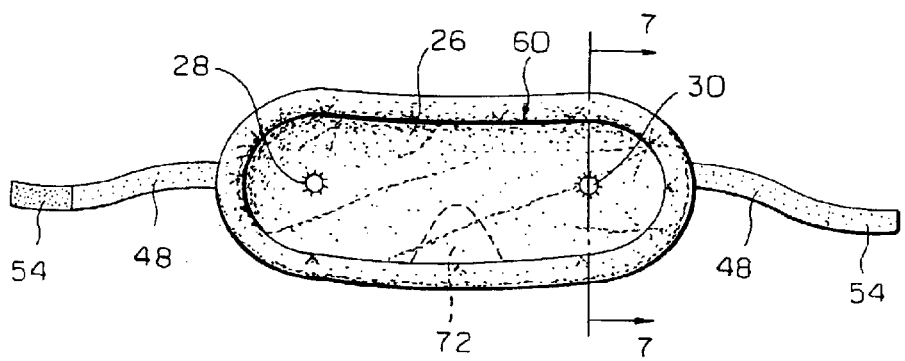
FIG. 6 is a perspective view showing the second eye shield separately.

In accordance with a preferred embodiment, the first eye shield 16 and second eye shield 26 are separable as is seen in FIGS. 5 and 6 and have pairs of straps 46 and 48, respectively, which are sown on opposite ends thereof. In a further preferred embodiment, the straps 46 on the opaque eye shield 16 have loop portions 50 of VELCRO® hook and loon fasteners 52 (see FIGS. 3 and 4) thereon while the straps 48 extending from the apertured eye shield 26 have hook portions 54 of the VELCRO® hook and loop fasteners 52 thereon. By having the VELCRO® hook and loon fasteners 52 joining the straps 46 and 48, the headband assembly 40 is readily adjustable for different head While the VELCRO® hook and loop fasteners 52 are preferred and illustrated, the couplings between the straps 46 and 48 may be of other configurations, such as buckles or snaps.

While in the preferred embodiment the straps 46 and 48 are separate, an another embodiment uses continuous elastic straps so that the headband assembly 40 adjusts readily to the size of the trainee's head.

Figure 7:
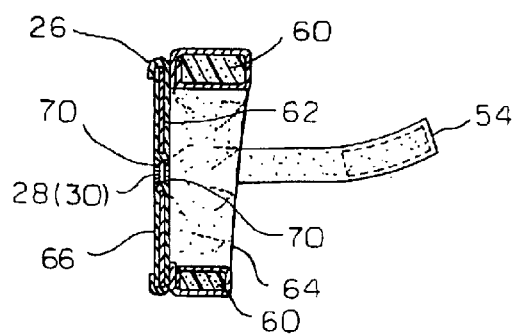
FIG. 7 is a side elevation of the second eye shield taken along line 7—7 of FIG. 6.

Referring now to FIG. 7, the apertured second eye shield 26 has a special configuration so that the apertures 28 and 30 are spaced from the trainee's eyes. This is accomplished by having a relatively thick padded rim 60 that abuts the trainee's face and surrounds the eyes. Stitched to the padded rim 60 is an assembly comprising a plastic stiffener 62 sandwiched between an inner fabric layer 64 and an outer fabric layer 66. The apertures 28 and 30 are formed through three layers, the inner fabric layer 64 being stitched around the apertures 28 and 30 to the outer fabric layer 66 by stitching 70. Stitching 70 within apertures 28 and 30 helps hold the stiffener 62 in place. The stiffener 62 also has a notch 72 therein, as shown in dotted lines in FIG. 6, which fits over the trainee's nose.

Preferably, both the opaque first eye shield 16 and the apertured second eye shield 26 are made of soft flexible fabric with the apertured eye shield being stiffened by the stiffener 62 so that the trainee is not distracted by discomfort caused by the eye shield assembly.

By having opaque first eye shield 16 and the apertured a second eye shield 26 connected together by the head strap assembly 40, the eye shields are always available to the trainee for changing visual conditions rapidly without having to stop and go on to a different eye shield. Accordingly, learning to cope with situations which cause visual impairment is enhanced by the eye shield assembly 10.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An eye shield assembly covering both eyes of a person during non-deadly force, martial arts, or firearms training, the assembly comprising:

a first eye shield which is opaque and covers both eyes to simulate complete blindness, the first eye shield having head strap portions extending from opposite ends thereof;

a second eye shield, the second eye shield having only two apertures therein, each aperature aligning with one eye to simulate tunnel vision; and head strap portions extending from opposite ends of the second eye shield, and the first and second eye shields individually covering the eyes separately with the eye shield not covering the eyes being a portion of a head band for the entire eye shield assembly, while the other eye shield covers the eyes.

2. The eye shield assembly of claim 1 wherein the head strap portions on the first eye shield and the head strap portions of the second eye shield cooperate to form an adjustable head strap arrangement.

3. The eye shield assembly of claim 2 wherein the head strap portions on the first eye shield and second eye shield are separate from one another and are joined by couplings.

4. The eye shield assembly of claim 3 wherein the couplings provide adjustable lengths for the head band portions.

5. The eye shield assembly of claim 4 wherein the couplings are hook and loop fasteners distributed along the headband portions.

6. The eye shield assembly of claim 1 wherein the headband is elastic.

7. The eye shield assembly of claim 1 wherein the second eye shield has a first section for positioning over one eye and a second section for positioning over the other eye and wherein there is a single aperture in each section.

8. The eye shield of claim 1 wherein the aperatures are circular.

9. The eye shield of claim 5 wherein the aperatures are circular.

10. The eye shield of claim 6 wherein the aperatures are circular.

11. The eye shield assembly of claim 5 wherein the second eye shield has a first section for positioning over one eye and a second section for positioning over the other eye and wherein there is a single aperture in each section.

12. The eye shield assembly of claim 6 wherein the second eye shield has a first section for positioning over one eye and a second section for positioning over the other eye and wherein there is a single aperture in each section.

13. The eye shield of claim 7 wherein the aperatures are circular.

* * * * *

UNITED STATES PATENT AND TRADEMARK OFFICE
CERTIFICATE OF CORRECTION

PATENT NO.    : 6,826,784 B2
DATED         : December 7, 2004
INVENTOR(S)   : Thomas J. Patire It is certified that error appears in the above-identified patent and that said Letters Patent is hereby corrected as shown below:

Title page,
Item [76], Inventors, delete "281 Rte. 46 West,"

Column 3,
Line 40, change "aperature" to -- aperture --; and

Column 4,
Lines 26, 28 and 30, change "aperatures" to -- aperatures --.
Line 40, change "aperatures" to -- apertures --.

Signed and Sealed this

Twenty-sixth Day of April, 2005

JON W. DUDAS
*Director of the United States Patent and Trademark Office*